United States Patent
Jacobs

(10) Patent No.: US 7,687,678 B2
(45) Date of Patent: Mar. 30, 2010

(54) ELECTRONIC BANDAGE WITH FLEXIBLE ELECTRONIC CONTROLLER

(75) Inventor: Philip Jacobs, Windham, NH (US)

(73) Assignee: Cisco Technology, Inc., San Jose, CA (US)

( * ) Notice: Subject to any disclaimer, the term of this patent is extended or adjusted under 35 U.S.C. 154(b) by 277 days.

(21) Appl. No.: 11/801,486

(22) Filed: May 10, 2007

(65) Prior Publication Data
US 2008/0281244 A1 Nov. 13, 2008

(51) Int. Cl.
*A61F 13/00* (2006.01)
(52) U.S. Cl. .................... 602/58; 602/41; 602/2
(58) Field of Classification Search .......... 602/2, 602/41–59; 604/289, 290, 304–308, 30, 604/67, 31, 35, 66; 128/DIG. 12, DIG. 13
See application file for complete search history.

(56) References Cited

U.S. PATENT DOCUMENTS

| | | | |
|---|---|---|---|
| 4,787,888 A | 11/1988 | Fox | |
| 5,693,016 A * | 12/1997 | Gumaste et al. | 604/131 |
| 5,772,688 A | 6/1998 | Muroki | |
| 6,283,931 B1 | 9/2001 | Augustine | |
| 6,317,630 B1 | 11/2001 | Gross et al. | |
| 6,421,561 B1 | 7/2002 | Morris | |
| 6,738,662 B1 * | 5/2004 | Frank | 604/20 |
| 6,974,224 B2 | 12/2005 | Thomas-Benedict | |
| 6,980,854 B2 | 12/2005 | Bernabei | |
| 7,304,201 B2 * | 12/2007 | Holloway et al. | 602/41 |
| 7,429,255 B2 * | 9/2008 | Thompson | 604/67 |

\* cited by examiner

*Primary Examiner*—Kim M Lewis
(74) *Attorney, Agent, or Firm*—BainwoodHuang

(57) ABSTRACT

An electronic bandage includes (i) bandage material, (ii) a treatment portion supported by the bandage material, the treatment portion being constructed and arranged to provide a treatment, and (iii) a flexible electronic controller supported by the bandage material. The flexible electronic controller combines with the bandage material and the treatment portion to form a conformable bandage which conforms to a treatment surface. The flexible electronic controller is constructed and arranged to dynamically control application of the treatment to the treatment surface while the conformable bandage conforms to the treatment surface. Such a bandage is capable of being packaged as a unitary body which is small, inexpensive and/or disposable.

22 Claims, 6 Drawing Sheets

ELECTRONIC BANDAGE WITH FLEXIBLE ELECTRONIC CONTROLLER

BACKGROUND

A conventional bandage is a strip of fabric or other material used as a protective covering for a wound or other injury. Such a bandage typically includes a glue-like material which sticks the fabric or other material to the wounded area thus preventing the conventional bandage from inadvertently detaching from the wound.

In contrast to a conventional bandage, a conventional portable medical device typically requires a strap, a garment or a user to hold the device to a wounded area or area under test. For example, the sensor of conventional fetal monitoring equipment typically requires fastening to a pregnant woman's abdomen via pinned straps or Velcro® ties for proper positioning. As another example, light therapy devices are often placed in a garment (e.g., a cap or sleeve) which must be worn or laid on in order for the light therapy devices to be properly positioned.

Furthermore, due to the bulkiness and largeness of the electronic circuitry associated with the portable medical devices, the typical design approach is to move the electronic circuitry out of the devices themselves and into external processing circuits (e.g., external computers). Typically, the external processing circuits require a separate housing in order to protect and support the processing circuits (e.g., a rigid container to enclose a delicate circuit board having mounted circuit board components, etc.).

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Overview

Figure 1:
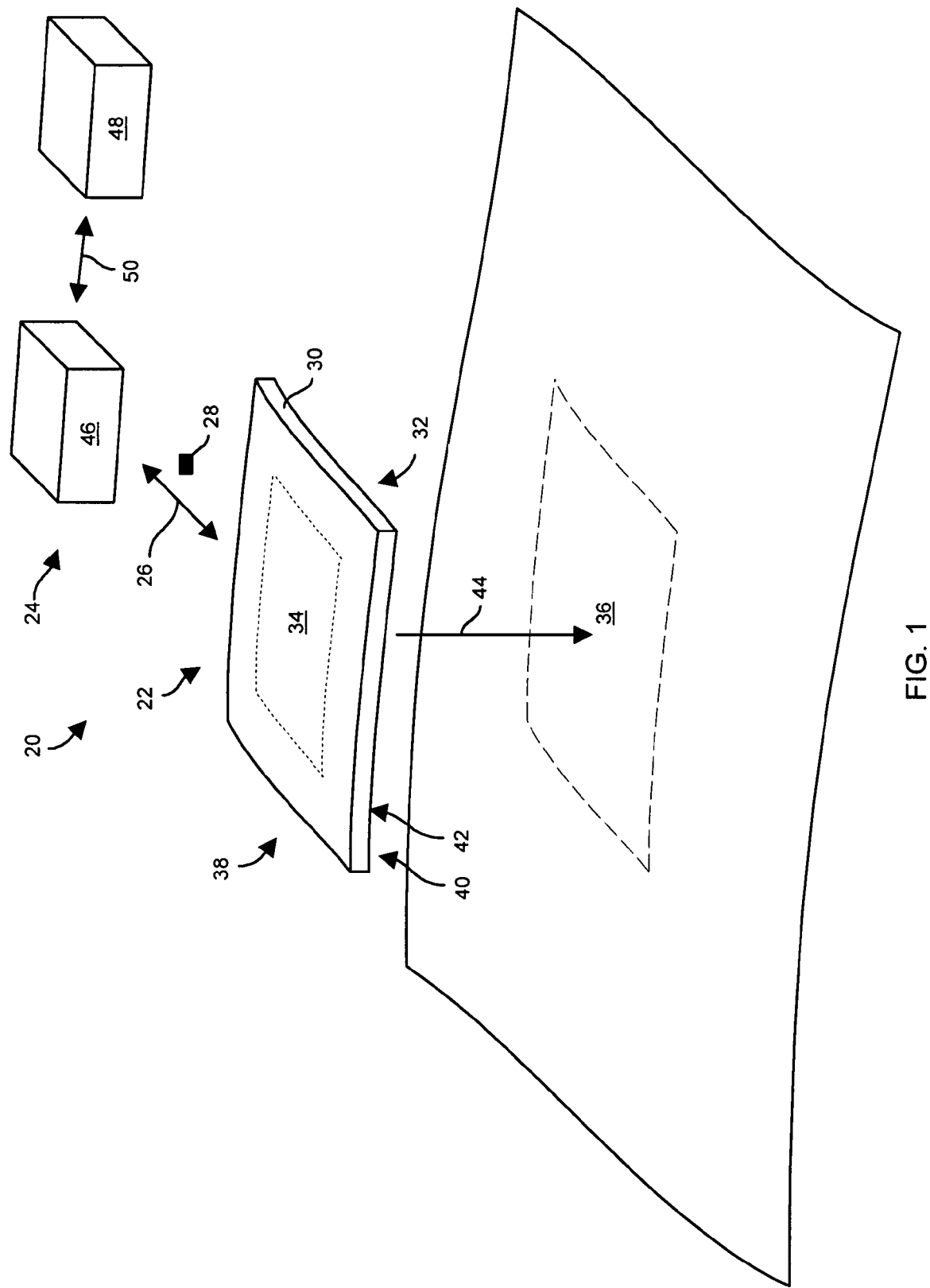
FIG. 1 is a perspective view of an electronic system having an electronic bandage which utilizes a flexible electronic controller.

Unfortunately, there are deficiencies to the above-described conventional bandage and conventional portable medical devices. For example, the above-described conventional bandage (i.e., a strip of fabric which covers an injury) is typically simple and limited in its utility. Along these lines, in the conventional bandage, there typically exists a non-sticky, gauze section which overlies the wound. In some instances, a person manually places medicine (e.g., cream or ointment) onto the gauze section or the wound prior to applying the conventional bandage. To further treat the wound, the person typically removes the bandage, cleans the wound, and then manually applies more medicine and a new bandage.

Additionally, in connection with the above-described conventional portable medical devices, the straps or garments which hold the devices properly in place are often cumbersome and uncomfortable due to the size and bulkiness of the devices themselves. Furthermore, the conventional portable medical devices are often re-used on other patients and thus require considerable care and cleaning after the devices are used. Moreover, in connection with conventional portable medical devices which use external processing circuits, the geometry of the external processing circuits (e.g., the weight and size the rigid container enclosing a delicate circuit board having mounted circuit board components) is not well-suited for being proximate to the devices. Rather, special connectors and/or cables are typically required to connect the conventional portable medical devices to the external processing circuits.

In contrast to the above-described conventional devices, an electronic bandage includes a flexible electronic controller which is capable of dynamically controlling application of a treatment to a treatment surface while conforming to the treatment surface. Such an electronic bandage is capable of being relatively small and lightweight thus adhering to the treatment surface without the need of straps, garments or a user to hold the bandage. Furthermore, such an electronic bandage is capable of including operative or active electronics (e.g., resistors, transistors, memory, etc.) thus alleviating the need for an external processing circuit. Rather, such an electronic bandage alone is well-suited for either open loop (non-adaptive) or closed loop (with feedback) operation. Moreover, the operation of the electronic bandage is augmentable with the addition of an external device (e.g., a data storage device, a higher powered diagnostic algorithms, etc.) if desired (e.g., via wireless communication), or with collaboration with other electronic bandages.

Such an electronic bandage is further capable of delivering multiple different treatments due to its programmability. These treatments may be programmed as a sequence of treatments which change due to events such as the passage of time, measured impact levels of previous treatments and current conditions, exhaustion of bandage resources or detection of conditions such as bleeding, among others. The programming of the bandages may be achieved by a combination of techniques. In one arrangement, the program is hard-coded into the electronic bandage and it thus not modifiable. In another arrangement, the program is loaded into the electronic bandage from a remote location thus enabling the program to be dynamically tailored while at the remote location to achieve the purposes of the treatments. In yet another arrangement, the program is a hybrid of hard-coding and loadable programming.

Additionally, it should be understood that the electronic bandage is not limited to use directly over a wounded area. Rather, the electronic bandage is capable of being used to monitor and treat the body through non-wounded areas using the optimal placement depending on the desired function.

One embodiment is directed to an electronic bandage (or plaster) which includes (i) bandage material, (ii) a treatment portion supported by the bandage material, the treatment portion being constructed and arranged to provide a treatment, and (iii) a flexible electronic controller (e.g., printed electronics) supported by the bandage material. The flexible electronic controller combines with the bandage material and the treatment portion to form a conformable bandage which conforms to a treatment surface. The flexible electronic controller is constructed and arranged to dynamically control application of the treatment to the treatment surface while the conformable bandage conforms to the treatment surface. Such a bandage is capable of being packaged as a unitary body which is small, inexpensive and/or disposable.

DESCRIPTION OF EXAMPLE EMBODIMENTS

FIG. 1 shows an electronic system 20 which includes an electronic bandage 22 and an optional augmentation assembly 24. The electronic bandage 22 and the augmentation assembly 24 communicate with each other through a communications medium 26 (e.g., copper wire, fiber optic cable, wireless medium, combinations thereof, etc.). In one arrangement, the electronic bandage 22 communicates with the augmentation assembly 24 via a wireless technology such as Bluetooth, Wi-Fi and the like (the signals being illustrated by the reference number 28).

The electronic bandage 22 includes bandage material 30, a treatment portion 32 and a flexible electronic controller 34. The bandage material 30 is constructed and arranged to support the treatment portion 32 and the flexible electronic controller 34. The treatment portion 32 is constructed and arranged to provide a treatment (e.g., deliver a drug, output light radiation, monitor a medical condition, etc.). The flexible electronic controller 34 is constructed and arranged to dynamically control application of the treatment to a treatment surface 36 (e.g., a wound, a portion of the body to receive medicine or to be sensed, etc.).

It should be understood that the flexible electronic controller 34 combines with the bandage material 30 and the treatment portion 32 to form a conformable bandage 38 which conforms to the treatment surface 36. In particular, due to flexibility of the various bandage components 30, 32, 34, the conformable bandage 38 is capable being implemented as a relatively thin, lightweight patch (see FIG. 1) which adheres to the treatment surface 36 via an adhesive 40 when placed over the treatment surface 36 (see the arrow 44). In some arrangements, the adhesive 40 extends around a periphery 42 of the comformable bandage 38. As a result of the dynamic features of the bandage, adaptive operations such as changing the amount of adhesion, modifying drug output, maintaining a constant elevated temperature, etc. are capable of being carried out entirely locally by the electronic bandage 22 without any participation by the optional augmentation assembly 24. Nevertheless, the augmentation assembly 24 is capable of provided to enhance operation and functionality.

As further shown in FIG. 1, the optional augmentation assembly 24 includes a communications device 46, an augmentation station 48 and a communications fabric 50. The augmentation station 48 enables a user to interface with the electronic bandage 22 remotely through the communications device 46 which operates as a communications relay between the augmentation station 48 and the electronic bandage 22. For example, the augmentation station 48 enables a user to, among other things, obtain status of the electronic bandage 22, measure and diagnose certain medical conditions of the treatment surface 36, store data and direct the operation of the electronic bandage 22. To this end, the augmentation station 48 is a computerized device having an I/O subsystem (e.g., mouse, keyboard and display), non-volatile storage (e.g., disk drive) and processing circuitry (e.g., a microprocessor running an operating system and a medical application-level program).

Furthermore, the communications device 46 is constructed and arranged to pass signals back and forth between the augmentation station 48 and the electronic bandage 22. In some arrangements, the communications medium 26 involves secure short-range radio frequency signals (e.g., Bluetooth), while the communications fabric 50 involves a different type of communications (e.g., a computer network, a bus, cellular telephone communications, communications through the Internet, etc.).

Figure 1A:
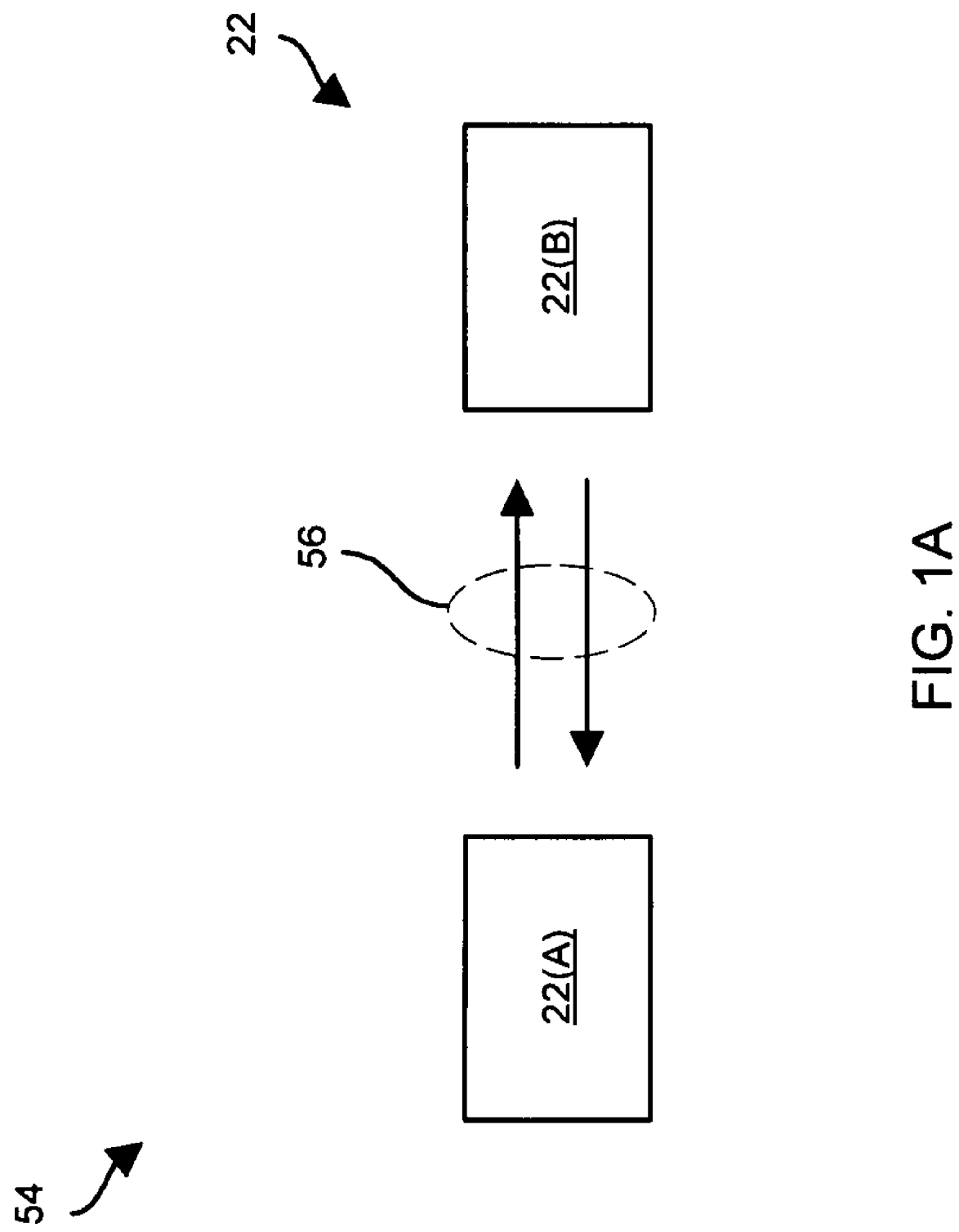
FIG. 1A is a block diagram of a collaborative situation among multiple electronic bandages.

FIG. 1A shows a collaborative situation 54 between multiple electronic bandages 22(A), 22(B) (collectively, electronic bandages 22). Although only two electronic bandages 22 are shown, it should be understood that the collaborative situation 54 is capable of including more than two electronic bandages 22 (e.g., three, four, etc.). It should be further understood that the electronic bandages 22 are capable of collaborating with each other using an exchange of signals 56 in a variety of arrangements.

In one arrangement, the electronic bandage 22(A) operates as a master controlling the operation of the electronic bandage 22(B) (and perhaps other bandages 22). Here, the electronic bandage 22(B) acts as a slave under control of the electronic bandage 22(A) by providing treatment and reporting back to the electronic bandage 22(A).

In another arrangement, each electronic bandage 22 acts as a peer to the other. In this arrangement, the collaboration among the electronic bandages 22 takes the form of sharing information and balancing resources. For example, the electronic bandage 22(A) may detect pain and signal this to the electronic bandage 22(B) which treats that pain. As another example, the electronic bandage 22(A) may run low on a particular resource such as power or a drug and, in such a condition, the electronic bandages 22 are capable of collaborating to maintain treatment by shifting the responsibility to treat from one bandage 22 to another, e.g., to the electronic bandage 22(B).

In yet another arrangement, the electronic bandages 22 are in communication with an augmentation device such as the augmentation assembly 24 of FIG. 1. Accordingly, the augmentation device is capable of coordinating treatment utilizing multiple electronic bandages 22. Further details will now be provided with reference to FIG. 2.

Figure 2:
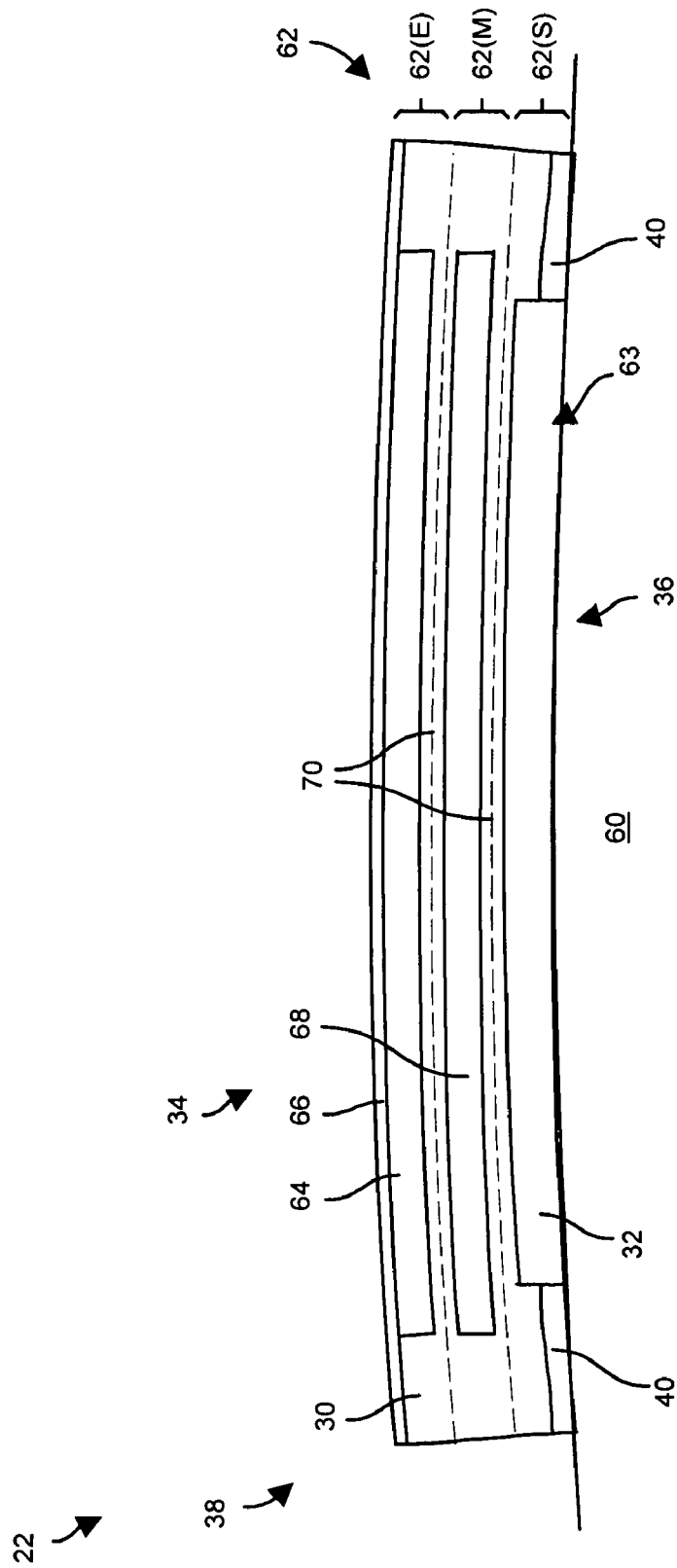
FIG. 2 is a detailed diagram of the electronic bandage of FIG. 1.

FIG. 2 shows a diagram of the electronic bandage 22. In particular, FIG. 2 provides a cross-sectional side view to illustrate the electronic bandage's ability to geometrically conform to the treatment surface 36, e.g., body tissue 60 having a wound and/or receiving therapy from the electronic bandage 22.

As shown in FIG. 2, the bandage has a multi-layer geometry (e.g., see the dashed lines in FIG. 2). In particular, the electronic bandage 22 has a treatment layer 62(S) (e.g., for sensors and actuators), a middle or intermediate layer 62(M) (e.g., for electronic controllers and memory storage), and an exposed layer 62(E) (e.g., for protection and display). Such layers 62(S), 62(M), 62(E) (collectively, layers 62) may be configured with additional layers above, below or in between depending on the particular application.

The treatment layer 62(S) is closest to the treatment surface 36. The treatment layer 62(S) includes the treatment portion 32 which was generally shown in FIG. 1 by the arrow 32. In some arrangements, the treatment layer 62(S) performs operations other than simply providing treatment, e.g., operates as a drug storage source 63.

The exposed layer 62(E) is furthest from the treatment surface 36. In some arrangements, the exposed layer 62(E) includes a portion 64 of the flexible electronic controller 34 to output information (e.g., visual data, a wireless signal, etc.). Preferably, the exposed layer 62(E) further includes protective material 66 to protect the various parts of the bandage. In some arrangements, the protective material 66 is a transparent, thermally conductive, permeable coating which enables a user to obtain visual data from the flexible electronic controller 34 while allowing the bandage to breathe (e.g., to release heat to the ambient air, to allow gas exchange, etc.).

The middle layer 62(M) interconnects the treatment layer 62(S) with the exposed layer 62(E). The middle layer 62(M) includes at least part 68 of the flexible electronic controller 34 which dynamically controls application of the treatment to the treatment surface 36.

It should be clear from FIG. 2 that support material 70 of the bandage material 30 resides in each layer to support the various bandage components and maintain the multi-layered structure of the bandage, e.g., the support material 70 forms a relatively strong, flexible and stretchable substrate enabling the adhesive 40 to adhere the bandage to the treatment surface 36 while the bandage conforms to the terrain of the treatment surface 36. By way of example only, the treatment surface 36 is shown as being bowed outwardly, and the material of the bandage enables the bandage to adapt its shape to mirror (or conform to) the treatment surface 36. Further details will now be provided with reference to FIG. 3.

Figure 3:
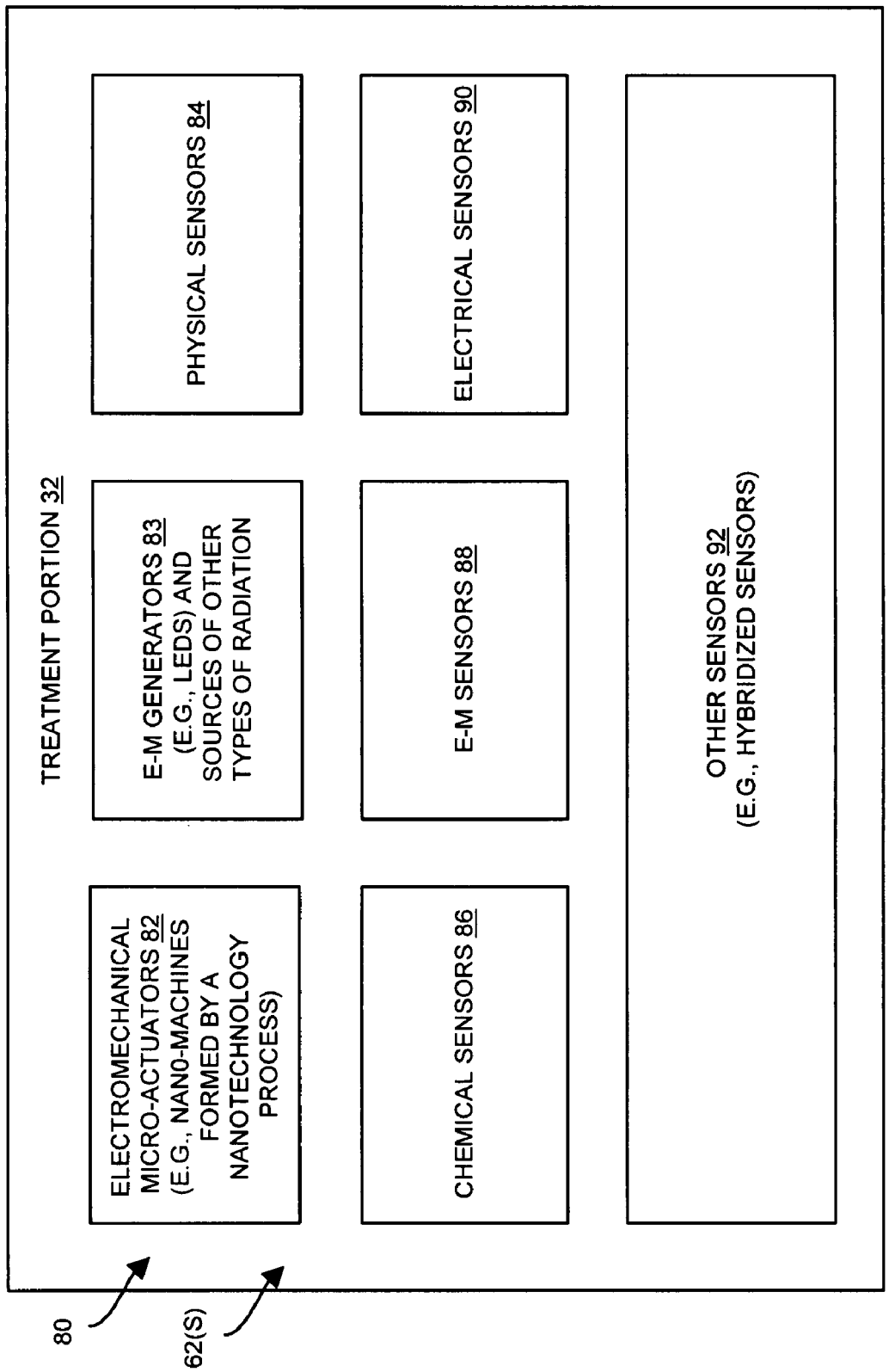
FIG. 3 is a block diagram of a treatment portion of the electronic bandage of FIG. 2.

FIG. 3 is a block diagram of various treatment components 80 which are capable of residing within the treatment portion 32 of the electronic bandage 22. During operation, the flexible electronic controller 34 is capable of providing control signals to and/or receiving data signals from these treatment components 80. It should be understood that a manufacturer is capable of including more than one treatment component 80 in particular implementations of the electronic bandage 22. However, there is no requirement that the manufacturer include multiple treatment components 80 in a particular implementation.

As shown in FIG. 3, the treatment portion 32 includes a set of electromechanical micro-actuators 82 which is mechanically supported by the support material 70 (FIG. 2) of the electronic bandage 22. The set of electromechanical micro-actuators 82 is constructed and arranged to deliver a treatment to the treatment surface 36 in response to adaptive feedback control from the flexible electronic controller 34.

In some arrangements, the micro-actuators 82 are nano-machines which are (i) formed by a nanotechnology process and (ii) constructed and arranged to apply the treatment to the treatment surface 36. In particular, the micro-actuators 82 receive electrical signals from the flexible electronic controller 34 and electromechanically dispense a drug from a drug storage source (e.g., a localized reservoir within the electronic bandage 22, also shown generally by the reference numeral 63 in FIG. 2) into the treatment surface 36 in response to the electrical signals. Alternatively, the drug storage source resides in a different level (e.g., in the middle layer 62(M) or in the exposed layer 62(E)).

The dosage or amount of the drug being delivered is capable of being controlled via micro-valves which change size in response to the electrical signals, electrophoresis, compression through needle-like ducts, diffusion, combinations thereof, and the like.

It should be understood that nano-machines (or nanites) are mechanical and/or electromechanical devices whose dimensions are measured in nanometers. Such a device is capable of being created through molecular manufacturing or printed electronics. One example is a machine (i.e., a sensor, a switch, an antenna, etc.) which is constructed and arranged to count specific molecules from a chemical source or sample.

In some arrangements, the micro-actuators 82 are constructed and arranged to electromechanically adjust a stretching tension provided by the electronic bandage 22. In these arrangements, the micro-actuators 82 are capable of controlling certain mechanical characteristics of the electronic bandage 22 such as the length and width, the stiffness, the amount of adhesion, and so on. The length and width are controllable via contracting and/or expanding axially-oriented micro-actuators in X and Y directions. The stiffness of the electronic bandage 22 is capable of being controlled by aligning or relaxing framing micro-actuators in response to the electrical signals. The amount of adhesion is capable of being controlled directly by actuating hook/loop-style micro-actuators, indirectly via changing the temperature of temperature sensitive micro-actuators via the electronic signals, or alternatively by releasing a second chemical which reduces the adhesive quality of a first chemical.

Other micro-actuator arrangements are also available including temperature control actuators, anti-adhesive actuators, vibration treatment, stimulation actuators, actuators which enhance absorption, and so on. An E-M generator 83 is capable of providing output such as electromagnetic treatment, heat treatment, light therapy and illumination, among others. In some arrangements, cooling is provided rather than heating treatment. Such cooling is capable of being achieved chemically or electrically (e.g., the Peltier effect).

In some arrangements, the treatment portion 32 further includes sensors which are distributed within the treatment layer 62(S) (FIG. 2) of the bandage. Depending on the particular application, the sensors are either (i) evenly patterned across the entire treatment layer 62(S) (e.g., to read the geometry of a healing wound), or focused towards the center or particular side and less at the periphery (e.g., to monitor temperature adjacent a wound or drug delivery site).

In some arrangements, the treatment layer 62(S) includes a set of physical sensors 84 which is mechanically supported by the support material 70 (FIG. 2) of the electronic bandage 22. The set of physical sensors 84 is constructed and arranged to measure various types of input and then output electrical signals to the flexible electronic controller 34. Such input includes heat, acceleration (e.g., due to coughing or other chest movement), stretch, humidity, shape and tension, among others.

In some arrangements, the treatment portion 32 includes a set of non-physical sensors such as chemical sensors 86, electromagnetic sensors 88, electrical sensors 90, and other types of sensors 92 (e.g., hybridized sensors). Such sensors are mechanically supported by the support material 70 (FIG. 2) of the electronic bandage 22, and are constructed and arranged to measure various types of input other than those measured by the physical sensors 86.

For many of these sensors, the input includes localized readings of vital signs (e.g., temperature, blood pressure, glucose levels, etc.), treatment surface properties, and/or environmental conditions among others such as measurement of chemical concentrations (e.g., blood oxygenation), infra-red signals, visual/color signals, wireless monitoring, body signals, electronic bandage signals, and so on. In some arrangements, communication among bandages is effectuated using the body to carry electrical signals. For certain sensors (e.g., the electrical sensors 90), the output is electrical and is provided to the flexible electronic controller 34. Nanostructures are well-suited for forming one or more of the sensors 84-92. Further details will now be provided with reference to FIG. 4.

Figure 4:
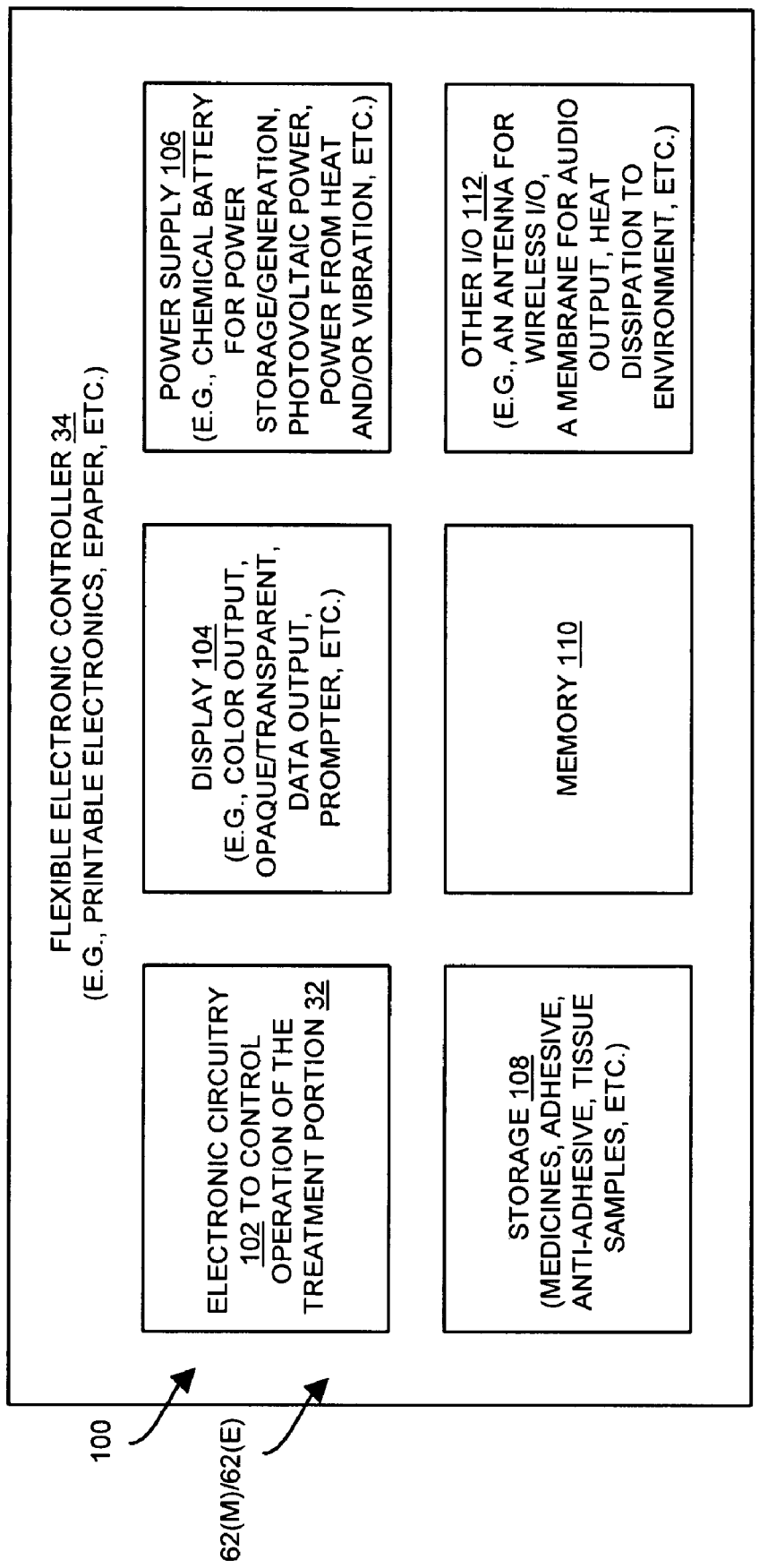
FIG. 4 is a block diagram of the flexible electronic controller of the electronic bandage of FIG. 2.

FIG. 4 is a block diagram of the flexible electronic controller 34 which provides control signals to and/or receives data signals from the treatment components 80 (FIG. 3). Various electronic components 100 of the flexible electronic controller 34 reside within the middle layer 62(M) and exposed layer 62(E) of the electronic bandage 22. Nothing precludes some of the flexible electronic controller 34 (e.g., display circuitry) from residing in the surface layer 62(S). It should be understood that a manufacturer is capable of including multiple electronic components 100 in particular implementations of the electronic bandage 22. However, there is no requirement that the manufacturer include multiple electronic components 100 in a particular implementation.

As shown in FIG. 4, the flexible electronic controller 34 includes electronic circuitry 102 which is in electrical communication with, and which is constructed and arranged to guide the operation of, the treatment portion 32 (FIG. 3). The electronic circuitry 102 is relatively lightweight and non-bulky and which is mechanically supported by the support material 70 (FIG. 2) of the electronic bandage 22. Technologies such as printable electronics (EP), electronic paper (or ePaper), other flexible and organic-based electronics, other thin film electronics, combinations thereof, and the like, are particularly well-suited for all or part of the electronic circuitry 102. The stretchable aspect of printable electronics makes printable electronics a well-suited choice for the electronic circuitry 102 in stretchable bandage applications. Additionally, the flexible, sunlight viewable and low cost aspects of ePaper make ePaper a well-suited choice for disposable bandage applications. As a result, electronic components such as resistors, transistors, diodes, memory cells, and the like are capable of being formed (e.g., via jetted ink in a reliable, consistent, low cost process) on a flexible paper-style medium for integration and electrical operation within the electronic bandage 22.

In some arrangements, the flexible electronic controller 34 further includes display circuitry 104 which is constructed and arranged to provide visual output. Again, technologies such as printable electronics, ePaper, and the like are well-suited for such circuitry. In some arrangements, the display circuitry 104 provides a chameleon function by matching the underlying skin color for aesthetic and/or camouflage purposes. In some arrangements, the display circuitry 104 selectively transitions between being opaque and transparent (e.g., in response to a switch or button press of a micro-actuator, touch or stretch programmed, etc.) to enable a user to view the treatment surface 36 underneath the bandage 22. In some arrangements, the display circuitry 104 provides data (e.g., color to identify infections or poor healing locations, etc.) or statistics (e.g., information regarding how long the bandage has in place, etc.) from the sensors of the treatment portion 32. In some arrangements, the display circuitry 104 prompts the user to take action (e.g., outputs a particular color to indicate that the drug source has been depleted). Other display operations and combinations of those described above are available as well.

In some arrangements, the flexible electronic controller 34 further includes a power supply 106 which is constructed and arranged to provide power to the flexible electronic circuitry 34. In some arrangements, the power supply 106 generates power (e.g., due to a chemical reaction). In some arrangements, the power supply 106 stores power from a main power feed (e.g., a rechargeable battery storing a charge). Gel, chemicals, or physical batteries are examples of power supplies which are capable of being used in these arrangements. In some arrangements, the power supply 106 derives power from the environment, e.g., the power supply 106 includes photovoltaic cells that respond to light and/or power generators that respond to heat and/or vibration.

In some arrangements, the flexible electronic controller 34 further includes material storage 108. In some arrangements, such storage source 108 includes multiple chemicals such as medicines, adhesive, anti-adhesive, etc. In some arrangements, the storage 108 is capable of collecting tissue material (e.g., chemicals from the skin for the purpose of later mixing and concentrating with other chemicals, chemical/bacterial/viral collection for chemical analysis following bandage removal, etc.).

In some arrangements, the flexible electronic controller 34 further includes a memory 110 which is constructed and arranged to store data. In some arrangements, the memory 110 is implemented using printable electronics, or the like and stores digital/binary information which is capable of being outputted to the augmentation assembly 24 (FIG. 1). The memory 110 is capable of being volatile storage (e.g., requiring periodic refreshing) or non-volatile storage (e.g., magnetically or flash based). Accordingly, data such as time, temperature, operating data, sensor measurements, etc. are available to the user.

In some arrangements, the flexible electronic controller 34 further includes other input/output (I/O) 112 which is constructed and arranged to receive input or provide output (e.g., EM input and output). In some arrangements, the other I/O 112 includes micro-actuators (e.g., switches, buttons, etc.) that receive commands from a user (e.g., the user presses certain locations of the electronic bandage 22 to control operation). In some arrangements, the other I/O 112 includes an antenna to facilitate wireless communications (e.g., command and data reception/transmission) between the electronic bandage 22 and the augmentation assembly 24, and/or among multiple electronic bandages 22. In some arrangements, the other I/O 112 includes a membrane, actuator, or resonator to provide audio or vibrational output, e.g., as therapy or signaling to a user. Additional components 100 for the electronic bandage 22 are available as well (e.g., electrical connectors, flexible cables, etc.). Further details will now be provided with reference to FIG. 5.

Figure 5:
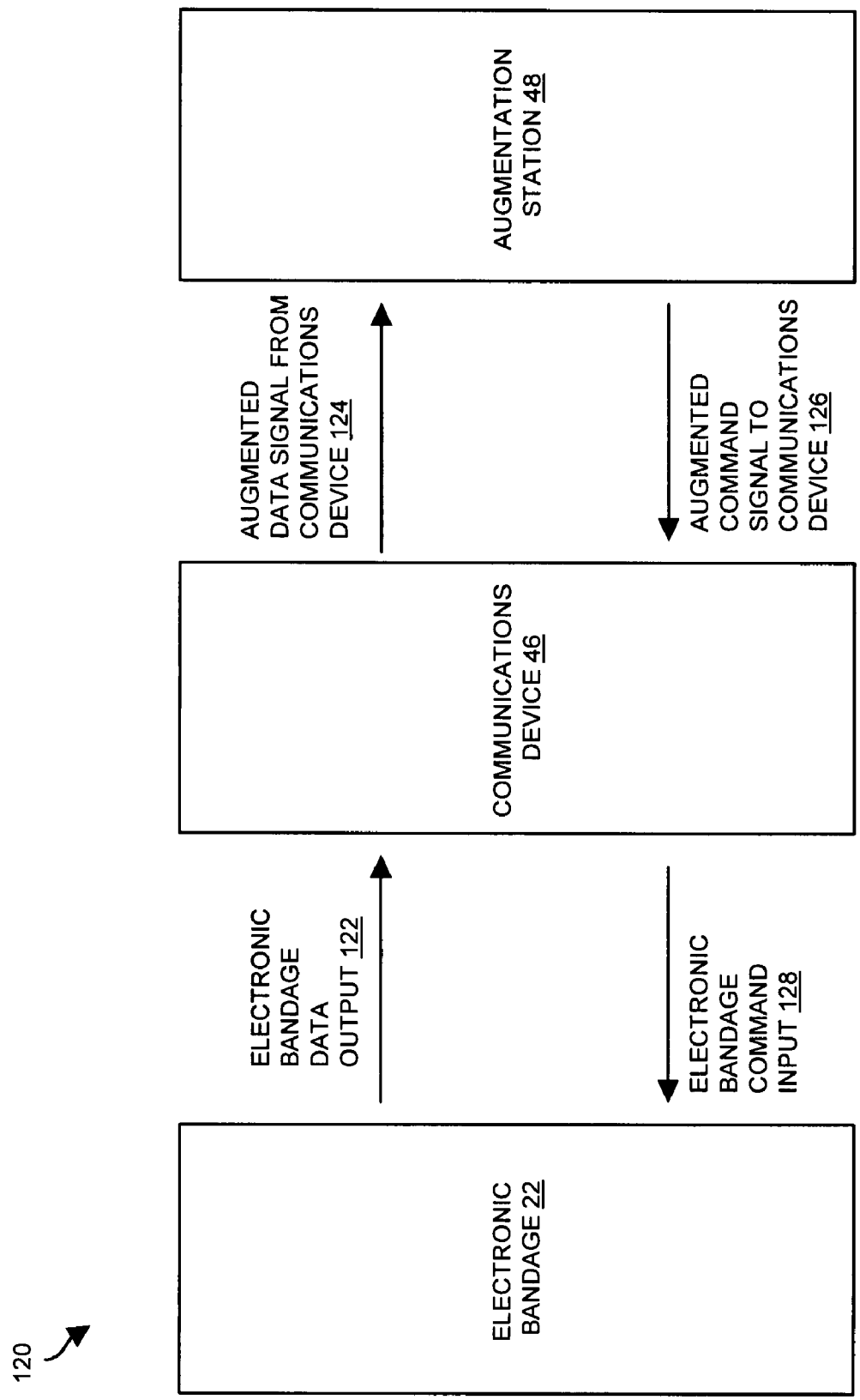
FIG. 5 is a block diagram of the electronic bandage of FIG. 2 in a closed loop application.

FIG. 5 is a block diagram of the electronic bandage 22 in a closed loop, adaptive application 120. Here, the electronic bandage 22 provides electronic bandage data output 122 (e.g., treatment data, operating state information, etc.) to the communications device 46. In order to minimize power consumption, the electronic bandage data output 122 is a short-range radio signal output in some arrangements (e.g., Bluetooth).

The communications device 46 of the augmentation assembly 24 (FIG. 1) receives the electronic bandage data output 122 and provides an augmented data signal 124 to the augmentation station 48. In some arrangements, the augmented data signal 124 includes the data contained within the electronic bandage data output 122 with enhancements (e.g., packets, frames or cells through a computerized network to the augmentation station 48).

The augmentation station 48 receives the augmented data signal 124 and stores the data contained within the signal 124. Additionally, the augmentation station 48 provides the ability to remotely control the operation of the electronic bandage 22. To this end, the augmentation station 48 provides an augmented command signal 126 containing commands to the communications device 46. Such transmission is capable of being carried out automatically such as by an automated program running on the augmentation station 48 thus enabling the system 20 to operate in an adaptive feedback manner. Alternatively, such transmission is capable of being carried out in response to direct instructions from a user (e.g., a physician or therapist) operating the augmentation station 48.

The communications device 46 then relays the commands to the electronic bandage 22 via electronic bandage command input 128 (e.g., a Bluetooth signal). In response, the electronic bandage 22 provides or modifies application of a treatment to the treatment surface 36 (FIG. 1). In some arrangements, the communications device 46 is a cell phone configured to communicate via Bluetooth with the bandage 22 and via cellular communications with the augmentation station 48.

It should be understood that the augmentation station 48 is further capable of processing raw data received from the electronic bandage 22. Accordingly, the augmentation station 48 is well-suited for marking progress of the treatment surface 36, diagnosing conditions of the treatment surface 36, and measuring the performance of the electronic bandage 22 itself (e.g., processing and storing data in a disk drive).

As mentioned above, an electronic bandage 22 includes a flexible electronic controller 34 which is capable of dynamically controlling application of a treatment to a treatment surface 36 while conforming to the treatment surface 36. Such an electronic bandage 22 is capable of being relatively small lightweight thus adhering to the treatment surface without the need of straps, garments or a user to hold the bandage. Furthermore, such an electronic bandage is capable of including operative or active electronics (e.g., resistors, transistors, memory, etc.) thus alleviating the need for an external processing circuit. Rather, such an electronic bandage alone is well-suited for either open loop (non-adaptive) or closed loop (with feedback). Nevertheless, the operation of the electronic bandage 22 is augmentable with the addition of an external device (e.g., a data storage device, a higher powered communications device, etc.) if desired (e.g., via wireless communication).

While various embodiments of the invention have been particularly shown and described, it will be understood by those skilled in the art that various changes in form and details may be made therein without departing from the spirit and scope of the invention as defined by the appended claims.

For example, the above-provided description explained the electronic bandage 22 in the context of a portable device which is capable of affixing to the skin. In some arrangements, the electronic bandage 22 (or multiple electronic bandages 22) is/are incorporated into another device such as bio-cot or a bio-bed for enhanced applications. Additionally, in some arrangements, the augmentation assembly 24 is portable and/or miniaturized into a "multi-corder" or "tri-corder" style implementation for greater maneuverability.

What is claimed is:

1. An electronic bandage, comprising:
bandage material;
a treatment portion supported by the bandage material, the treatment portion being constructed and arranged to provide a treatment; and
a flexible electronic controller supported by the bandage material, the flexible electronic controller combining with the bandage material and the treatment portion to form a conformable bandage which conforms to a treatment surface, the flexible electronic controller being constructed and arranged to dynamically control application of the treatment to the treatment surface while the conformable bandage conforms to the treatment surface;
wherein the bandage material includes:
support material which supports the treatment portion and the flexible electronic controller, and
an adhesive substance in communication with the support material, the adhesive substance being constructed and arranged to adhere the support material to the treatment surface; and
wherein the treatment portion includes:
a set of electromechanical micro-actuators which is mechanically supported by the support material, the set of electromechanical micro-actuators being constructed and arranged to deliver the treatment to the treatment surface in response to adaptive feedback control from the flexible electronic controller.

2. An electronic bandage as in claim 1 wherein the flexible electronic controller is constructed and arranged to electronically collaborate via electronic signals with another electronic bandage to perform an augmented treatment operation.

3. An electronic bandage as in claim 1 wherein the set of electromechanical micro-actuators includes:
nano-machines which are (i) formed by a nanotechnology process and (ii) constructed and arranged to apply the treatment to the treatment surface.

4. An electronic bandage as in claim 1 wherein the set of electromechanical micro-actuators is further constructed and arranged to electromechanically adjust a stretching tension provided by the electronic bandage.

5. An electronic bandage as in claim 1 wherein the set of electromechanical micro-actuators, when delivering the treatment to the treatment surface, is constructed and arranged to electromechanically dispense a drug to the treatment surface.

6. An electronic bandage as in claim 1 wherein the treatment portion further includes:
a set of physical sensors which is constructed and arranged to detect a physical medical condition of the treatment surface during application of the treatment to the treatment surface.

7. An electronic bandage as in claim 1 wherein the treatment portion further includes:
a set of chemical sensors which is constructed and arranged to detect a chemical composition of the treatment surface during application of the treatment to the treatment surface.

8. An electronic bandage as in claim 1 wherein the flexible electronic controller is implemented using printed electronics; and
wherein the printed electronics of the flexible electronic controller includes circuitry which is constructed and arranged to electronically or chemically adjust an amount of adhesion provided by the adhesive substance when adhering the support material to the treatment surface.

9. An electronic bandage as in claim 8 wherein the treatment portion further includes:
a chemical store which stores a set of chemicals for use at the treatment surface.

10. An electronic bandage, comprising:
bandage material;
a treatment portion supported by the bandage material, the treatment portion being constructed and arranged to provide a treatment; and
a flexible electronic controller supported by the bandage material, the flexible electronic controller combining with the bandage material and the treatment portion to form a conformable bandage which conforms to a treatment surface, the flexible electronic controller being constructed and arranged to dynamically control application of the treatment to the treatment surface while the conformable bandage conforms to the treatment surface;
wherein the conformable bandage formed by the flexible electronic controller, the bandage material and the treatment portion defines a multi-layered structure with (i) the treatment portion substantially residing in a first layer, (ii) a protective material residing in an exposed layer, and (iii) the flexible electronic controller residing in an intermediate layer disposed between the first layer and the exposed layer.

11. An electronic bandage as in claim 10 wherein the flexible electronic controller includes:
   electronic circuitry which is formed out of printable electronics and which is in electrical communication with the treatment portion substantially residing in the first layer.

12. An electronic bandage as in claim 11 wherein the flexible electronic controller further includes:
   a chemical battery which substantially resides in the intermediate layer and which is configured to provide power to the electronic circuitry.

13. An electronic bandage as in claim 11 wherein the electronic circuitry formed out of the printable electronics includes:
   digital memory which is constructed and arranged to store data in a digital manner.

14. An electronic bandage as in claim 11 wherein the electronic circuitry formed out of the printable electronics includes:
   an antenna; and
   transmit circuitry coupled to the antenna, the transmit circuitry being constructed and arranged to provide wireless output from the electronic bandage and an external device through the antenna.

15. An electronic bandage as in claim 14 wherein the electronic circuitry formed out of the printable electronics further includes:
   receive circuitry coupled to the antenna, the receive circuitry being constructed and arranged to obtain wireless input from the external device through the antenna.

16. An electronic bandage as in claim 10 wherein the flexible electronic controller includes:
   a visual display which is formed of electronic paper which is viewable through the protective material residing in the exposed layer.

17. An electronic bandage as in claim 10 wherein the flexible electronic controller includes:
   an E-M generator which is constructed and arranged to output E-M radiation to the treatment surface.

18. An electronic bandage as in claim 10 wherein the exposed layer is constructed and arranged to conduct heat from the flexible electronic controller and release that heat into ambient air.

19. An electronic bandage as in claim 10 wherein the flexible electronic controller is constructed and arranged to electronically collaborate via electronic signals with another electronic device to perform an augmented treatment operation.

20. An electronic bandage as in claim 10 wherein the bandage material includes:
   support material which supports the treatment portion and the flexible electronic controller; and
   an adhesive substance in communication with the support material, the adhesive substance being constructed and arranged to adhere the support material to the treatment surface.

21. An electronic bandage system, comprising:
   an electronic bandage which includes (i) bandage material, (ii) a treatment portion supported by the bandage material, the treatment portion being constructed and arranged to provide a treatment, and (iii) a flexible electronic controller supported by the bandage material, the flexible electronic controller combining with the bandage material and the treatment portion to form a conformable bandage which conforms to a treatment surface, the flexible electronic controller being constructed and arranged to dynamically control application of the treatment to the treatment surface while the conformable bandage conforms to the treatment surface,
   wherein the conformable bandage formed by the flexible electronic controller, the bandage material and the treatment portion defines a multi-layered structure with (i) the treatment portion substantially residing in a first layer, (ii) a protective material residing in an exposed layer, and (iii) the flexible electronic controller residing in an intermediate layer disposed between the first layer and the exposed layer; and
   an external augmenting device in wireless communication with the electronic bandage, the external augmenting device being constructed and arranged to receive and store data from the flexible electronic controller of the electronic bandage, and provide instructions to the flexible electronic controller of the electronic bandage.

22. An electronic bandage system as in claim 21 wherein the bandage material of the electronic bandage includes:
   support material which supports the treatment portion and the flexible electronic controller; and
   an adhesive substance in communication with the support material, the adhesive substance being constructed and arranged to adhere the support material to the treatment surface.

* * * * *